(12) United States Patent
White et al.

(10) Patent No.: US 7,850,692 B2
(45) Date of Patent: Dec. 14, 2010

(54) MINIMALLY INVASIVE SURGICAL REAMER AND CONNECTION

(75) Inventors: Patrick Michel White, West Chester, PA (US); André Lechot, Orvin (CH); Ezzedine Mahmoud, Bienne (CH)

(73) Assignee: Greatbatch Medical S.A., Orvin (CH)

( * ) Notice: Subject to any disclaimer, the term of this patent is extended or adjusted under 35 U.S.C. 154(b) by 1018 days.

(21) Appl. No.: 10/510,934

(22) PCT Filed: Aug. 1, 2002

(86) PCT No.: PCT/US02/21310

§ 371 (c)(1),
(2), (4) Date: May 20, 2005

(87) PCT Pub. No.: WO03/086208

PCT Pub. Date: Oct. 23, 2003

(65) Prior Publication Data

US 2005/0203525 A1     Sep. 15, 2005

Related U.S. Application Data

(60) Provisional application No. 60/372,285, filed on Apr. 12, 2002.

(51) Int. Cl.
*A61B 17/00* (2006.01)
(52) U.S. Cl. .................. 606/81; 606/79
(58) Field of Classification Search ............ 606/79–85, 606/99, 167, 171, 180, 183, 86 R, 91; 60/79–85
See application file for complete search history.

(56) References Cited

U.S. PATENT DOCUMENTS 3,702,611 A    11/1972   Fishbein 4,023,572 A *  5/1977   Weigand et al. ............... 606/81

(Continued)

FOREIGN PATENT DOCUMENTS

DE        7113620        9/1971

(Continued)

OTHER PUBLICATIONS

International Search Report in SN PCT/US02/21310.

(Continued)

*Primary Examiner*—Thomas C Barrett
*Assistant Examiner*—Matthew Lawson
(74) *Attorney, Agent, or Firm*—Michael F. Scalise

(57)    ABSTRACT

An acetabular reamer has a cutting structure rotatable about a longitudinal axis with a domed shell portion. The shell has an outer surface presenting multiple cutting sites and an inner surface for accumulation of debris. The shell has a static insertion profile area that is defined by a pair of first curved portions generated about a first radius with a center that lies on the axis and a pair of second curved portions generated about a center spaced apart from the axis. The cutting structure has a circular dynamic profile area generated upon rotation of the reamer by a handle. Both the static insertion area and dynamic profile area lie transferase to the axis, the former being smaller than the latter. Several distinctive alignment structures are described, alone and in combination with reamers having a conventional hemispherical shell, as well as in combination with present reamers that are less invasive.

18 Claims, 15 Drawing Sheets

U.S. PATENT DOCUMENTS

| | | | |
|---|---|---|---|
| 4,199,284 A * | 4/1980 | Kress et al. | 408/233 |
| 4,239,427 A * | 12/1980 | Walton, II | 408/213 |
| 4,811,632 A * | 3/1989 | Salyer | 76/115 |
| 5,098,437 A * | 3/1992 | Kashuba et al. | 606/89 |
| 5,100,267 A * | 3/1992 | Salyer | 407/54 |
| 5,417,696 A * | 5/1995 | Kashuba et al. | 606/91 |
| 5,658,290 A * | 8/1997 | Lechot | 606/80 |
| 5,913,858 A * | 6/1999 | Calandruccio et al. | 606/79 |
| 5,976,144 A * | 11/1999 | Fishbein et al. | 606/80 |
| 5,980,170 A * | 11/1999 | Salyer | 408/239 R |
| 6,063,124 A | 5/2000 | Amstutz | |
| 6,100,536 A * | 8/2000 | Ito et al. | 250/492.21 |
| 6,102,915 A * | 8/2000 | Bresler et al. | 606/80 |
| 6,106,536 A | 8/2000 | Lechot | |
| 6,129,732 A * | 10/2000 | Lechot | 606/80 |
| 6,168,600 B1 | 1/2001 | Grace et al. | |
| 6,245,074 B1 * | 6/2001 | Allard et al. | 606/80 |
| 6,264,647 B1 | 7/2001 | Lechot | |
| 6,283,972 B1 | 9/2001 | Riley | |
| 6,312,325 B1 * | 11/2001 | Van Osenbruggen | 451/548 |
| 6,475,221 B1 | 11/2002 | Fishbein et al. | |
| 6,702,819 B2 * | 3/2004 | Lechot | 606/80 |
| 6,916,342 B2 * | 7/2005 | Frederick et al. | 623/22.29 |
| 7,090,678 B2 * | 8/2006 | Cotting et al. | 606/81 |
| 2002/0010470 A1 * | 1/2002 | Lechot | 606/80 |
| 2002/0099380 A1 * | 7/2002 | Salyer et al. | 606/80 |
| 2003/0220647 A1 * | 11/2003 | McCallum et al. | 606/81 |
| 2004/0049199 A1 | 3/2004 | Lechot et al. | |
| 2005/0216020 A1 * | 9/2005 | Orton | 606/80 |

FOREIGN PATENT DOCUMENTS

| | | | |
|---|---|---|---|
| EP | 0 893 097 A2 * | 1/1999 | 606/80 |
| WO | WO 99/47051 | 9/1999 | |
| WO | WO 02/49517 A1 | 6/2002 | |

OTHER PUBLICATIONS

Supplemental European Search, dated Sep. 23, 2010.

* cited by examiner

Fig.20
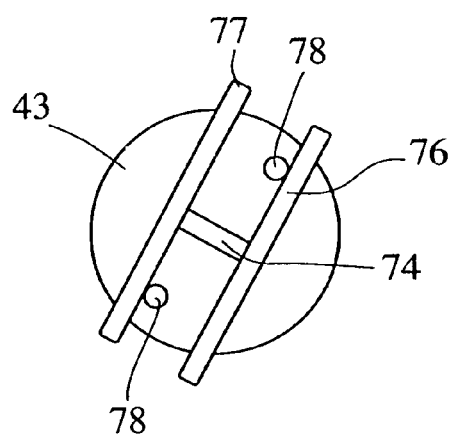
Fig.21
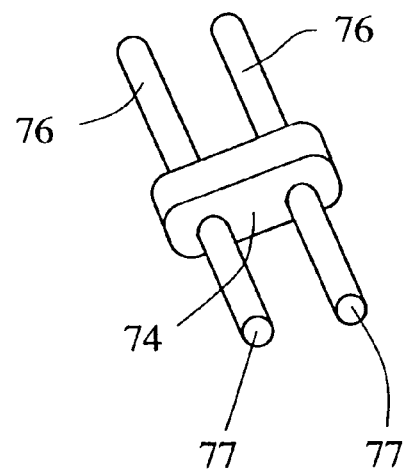
Fig.22
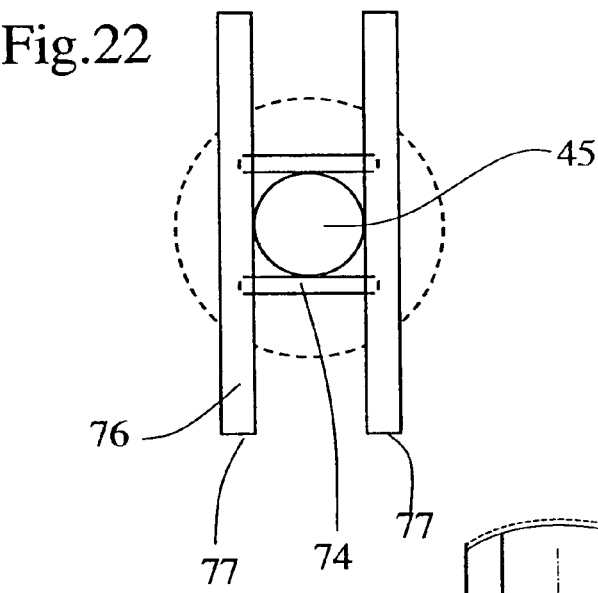
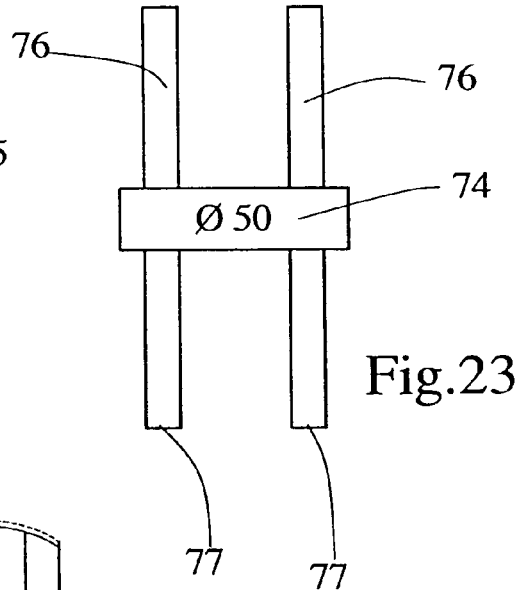
Fig.23
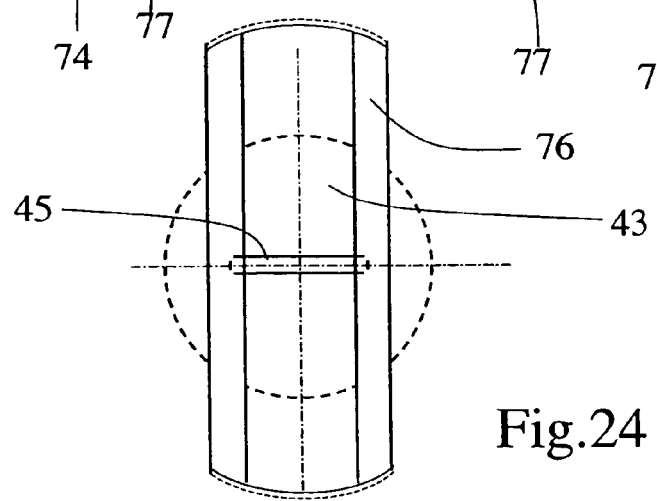
Fig.24

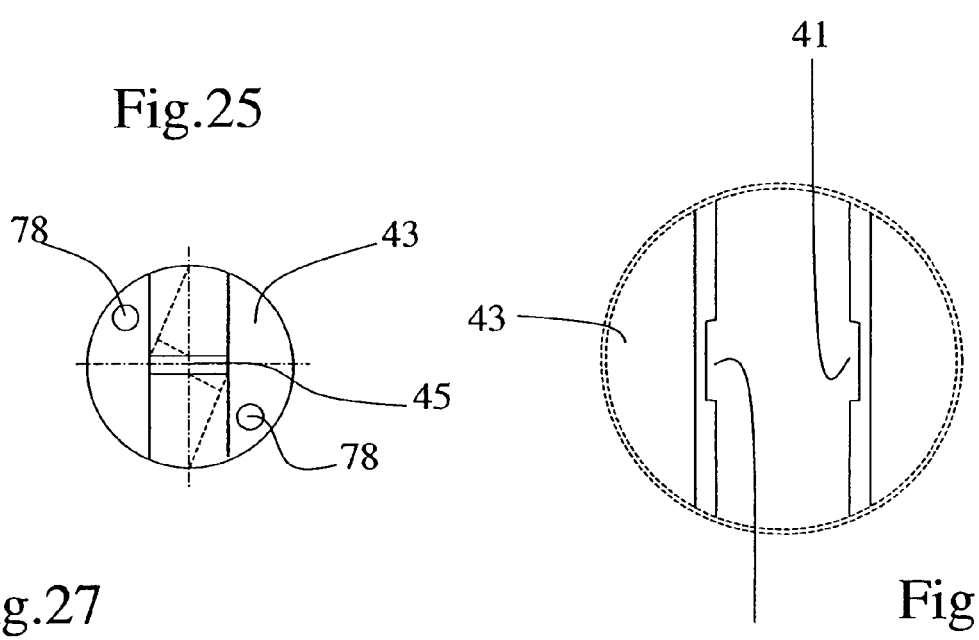
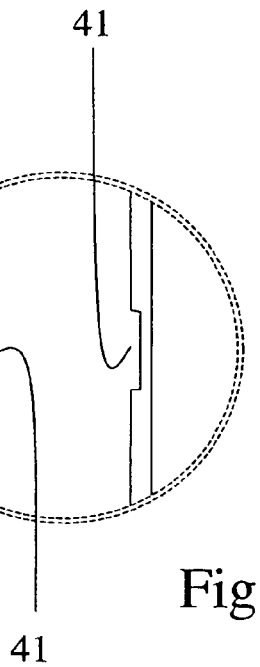
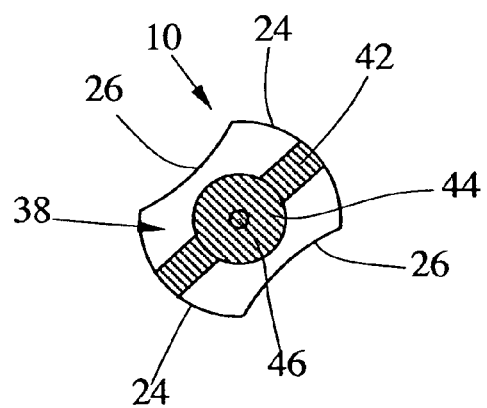
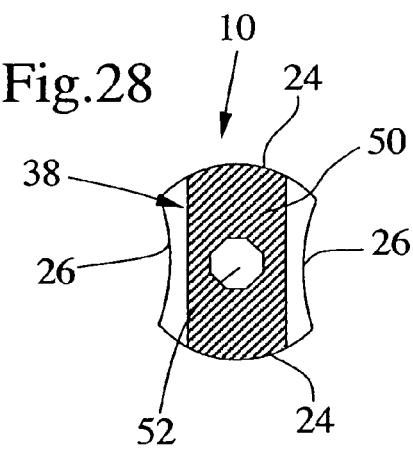
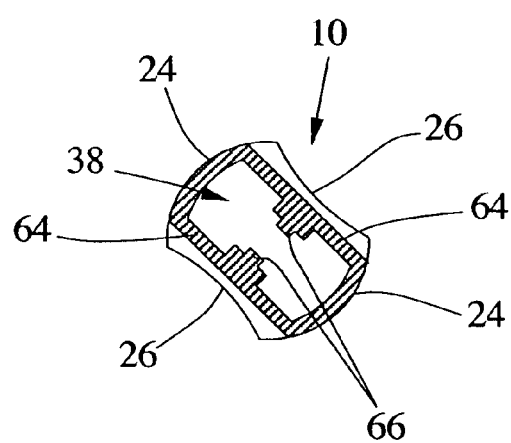

MINIMALLY INVASIVE SURGICAL REAMER AND CONNECTION

CROSS-REFERENCE TO RELATED APPLICATIONS

This application is a National Stage Entry of PCT/US02/21310, filed Aug. 1, 2002, which claims priority from U.S. Provisional Application Ser. No. 60/372,285, filed Apr. 12, 2002.

TECHNICAL FIELD

This invention generally relates to surgical reaming assemblies, particularly those having a domed-shape cutting tool adapted to shape a bone cavity, such as an acetabulum, for receiving an implantable prosthesis.

BACKGROUND OF THE INVENTION

An objective of orthopedic surgery is to continue developing improved devices and methods that are less invasive to the patient. These efforts include minimizing the incision required to employ surgical instrumentation in the preparation of a bone cavity or socket to receive an implant in, e.g., an acetabular reaming procedure. A way to minimize the incision is to optimize the geometry that the reamer presents to the incision, characterized herein as its "static insertion profile area". By simplifying the surgical steps required, the reamer design can further lessen total inter-operative time and hence decrease the risks generally associated with longer surgical times.

The present inventors have previously disclosed hollow domed acetabular reamers with hemispherical shapes, e.g., PCT/US99/05951 and U.S. Pat. Nos. 5,658,290 and 6,264,647, which are assembled to driving handles for controlled rotation about a cut axis during the reaming operation. Such prior art acetabular reamers present a circular static insertion profile area (with no straight sides) to the surgical incision, generating a circular dynamic profile area upon rotation of the reamer in the bone socket. A cotyloid reamer of one of the present inventors is shown in U.S. Pat. No. 6,106,536 having a much different i.e., lop-sided construction compared to the inventors' prior acetabular reamers. This cotyloid reamer presents a semi-circular static insertion profile area (i.e., one straight side) to the surgical incision, which is less than the circular dynamic profile area generated upon rotation of the reamer in the bone.

The entire contents of the present inventors' above-identified prior patent documents are entirely incorporated by reference herein and relied-upon.

Another approach taken by others, discussed below in conjunction with FIGS. 1-3 herein, has been to use an acetabular reamer of the above domed type, modified with straight sides, for purposes of a less invasive surgical procedure. Such reamers present a partially circular static insertion profile area to the surgical incision, which is defined by a pair of curved sides generated about a center coinciding with the rotational axis, separated by a pair of straight sides. Notwithstanding, it would still be beneficial to provide a reamer having a static insertion profile area that results in a less invasive reaming operation, in terms of minimized time through efficiency, as well as a minimized incision size.

Another objective of orthopedic surgery is to develop instrumentation that is more handily and efficiently used while accurately maintaining a precise cut of the bone socket, in order to minimize inter-operative time. The inventors' above-incorporated patent documents also discuss various alternative connections by which their reamers may be assembled to a handle, such assemblies including alignment structures on the reamer and handle allowing controlled rotation of the reamer in the bone socket. Such assembly mechanisms have included a reamer having a bar with centering hole and a bar with a centering boss. The inventors have also taught reamers having an alignment structure with a pair of bars mounted either in orthogonal intersecting relationship or extending chordally in parallel, for assembly with e.g., a bayonet catch or other structure(s) of the handle. The present inventors believe that the above-mentioned prior reamer-handle connections would, nevertheless, be further beneficial when used in reamers having a less invasive static insertion profile area.

Accordingly, it would still be desirable to reduce the static insertion profile area of the reamer to minimize the size of the surgical incision, while providing a precise cut of the desired bone cavity.

It would also be desirable to have connections between a reamer and handle that are designed to perform with a less invasive reamer geometry. It would further be desirable to have novel connections that function with different handles having a variety of bayonet or other assembly connections, regardless of reamer geometry.

It would further be desirable to provide a novel reamer tool-handle connection in either a conventional or a less invasive geometry, which allows bone and other organic matter trapped in the reamer, to more effectively be removed.

SUMMARY OF THE INVENTION

According to one aspect of the present invention, there is provided a surgical reamer for cutting a bone socket. The reamer has a cutting structure rotatable about a longitudinal axis, with a domed shell portion having an outer surface presenting multiple cutting sites and an inner surface for accumulation of debris. The shell has a static insertion profile area being defined by a first curved portion generated about a first radius with a center that lies on the axis and a second curved portion generated about a center that is spaced apart from the axis. The cutting structure has a preferably circular dynamic profile area generated upon rotation of the reamer, such as by a handle driven from a power source. Both static insertion and dynamic profile areas lie transverse to the axis, with the static insertion profile area being smaller than the dynamic profile area.

In a preferred embodiment of the invention, a pair of second curved portions is situated in opposed relationship from one another with respect to the shell. The pair of second curved portions may be either concave or convex, relative to the rotational axis; moreover, the curvature geometry may be described as circular or parabolic. The number of second curved portions may be 2, 4 or some other even number, preferably corresponding to the number of first curved portions noted above, with the pair(s) of first curved portions being separated from one another by the pair(s) of second curved portions, respectively. Thus the cutting structure may present a partially circular convex or concave static insertion profile area, where one pair of first and one pair of second curved portions is provided, or it may present a cruciform static insertion profile area where two pairs of first and second curved portions are chosen by design. A convex static insertion profile area is more beneficial in terms of introducing the reamer through a less invasive surgical incision, whereas a concave static insertion profile area is designed for easier extraction of the reamer from the incision.

In another preferred embodiment of the invention, the shell has a partially hemispherical domed 3-dimensional shape with an apex and a pair of first curved portions that respectively define a pair of diametrically opposed base portions spaced from the apex. It is further alternatively preferred that the base portions may be banded and include bladed portions to facilitate the reaming of a fully hemispherical, i.e., acetabular, bone cavity.

In a more preferred embodiment of the above inventive aspect, a pair of first curved portions is provided, describing a diameter of the domed shell portion that is co-linear with the first radius, the pair of first curved portions being situated in diametrically opposed relationship to one another. The number of first curved portions is two or four, as is the number of second curved portions, respectively. The second curved portions are either concave or convex, with respect to one another. The second curved portions are either circular or parabolic in curvature. The dynamic profile area of the reamer is circular.

According to another aspect of the present invention, the shell preferably defines a partially hemispherical, domed structure having an apex aligned with the rotational axis. The dome or other functional elements of the shell may be a unitary plate or a combination of plates. The shell has a pair of first curved portions that respectively define a pair of diametrically opposed base portions spaced from the apex. A mounting means preferably is an alignment structure extending between the base portions, which assembles with a handle for controlled rotation of the reamer. The handle more preferably has a bayonet catch mechanism for receiving the alignment structure. The alignment structure may be a single bar with a centering boss, which can optionally include a central aperture.

Alternatively, the alignment structure may be a plate with keyed centering aperture.

Also alternatively, the alignment structure may be a bar having opposed terminal ends fixed at the base portions, respectively, including a cross-member having opposed free ends and being of a lesser length than the bar. The cross-member intersects the bar at the axis to define a cruciform shape presenting the bars to be assembled with the handle, while allowing removal of debris adjacent the free ends of the cross-member.

Still alternatively, the alignment structure may be a pair of bars spaced from one another on either side of the axis, with a pair of keyed male centering members projecting inwardly from the bars toward the axis, respectively.

There is alternatively preferred an alignment structure provided with a pair of bars each having opposed terminal ends, adjacent ends of the respective bars being spaced from one another along each base portion, including a centering structure located on the pair of bars for attachment to the handle. The centering structure may preferably be a cross-member, which is affixed together with the pair of bars and forms an H-shape for receiving, between the bars, one or more longitudinal pins from a bayonet catch more preferably provided on the handle. The alignment structure may also preferably be a pair of curved bars that is each more preferably formed in an S-shape, the bars being non-intersecting and together presenting a generally Y-shaped or hourglass configuration allowing the bars to be assembled directly with the handle using bayonet catches that are further preferred. Preferably, a shaft is provided having a fixed end joined to the bars and extending along the rotational axis longitudinally toward the handle. The shaft has a free end with radial spokes for assembly with the handle, more preferably by corresponding bayonet catches on the handle.

According to a further aspect of the present invention, a surgical reaming assembly includes a hollow reamer body having a wall portion with an external surface, a pair of opposed base portions and an apex defining a cut axis. The wall defines a central cavity and a plurality of passageways through the wall presenting cutting sites. The passageways communicate between the external surface of the wall and the central cavity, for passage of removed bone and tissue through the wall into the central cavity. A holder is provided for transmitting torque to the reamer body, for rotation of the reamer body about the cut axis. An alignment structure provided on the body for assembly with the handle, including a first bar extending between the base portions and a second bar that intersects the first bar along the cut axis. The second bar further includes opposed free ends and has a shorter length than the first bar to allow removal of debris there around, the bars together forming a cruciform shape allowing the bars to be assembled with the handle for controlled rotation of the reamer body.

According to yet a further aspect of the present invention, a surgical reaming assembly includes a hollow reamer body having a wall portion with an external surface, a pair of opposed base portions and an apex defining a cut axis. The wall defines a central cavity and a plurality of passageways through the wall presenting cutting sites. The passageways communicate between the external surface of the wall and the central cavity for passage of removed bone and tissue through the wall into the central cavity. A holder is provided for transmitting torque to the reamer body about the cut axis. An alignment structure is provided for assembling the reamer body to the handle, having a pair of non-intersecting curved bars each extending between fixed ends respectively located on the opposed base portions. The bars converge in a direction toward the cut axis and are attached to the handle for controlled rotation of the reamer body.

According to still a further aspect of the present invention, a surgical reaming assembly includes a hollow reamer body having a wall with an external surface, a base and an apex defining a cut axis. The wall contains a central cavity and has a plurality of passageways through the wall presenting cutting sites. The passageways communicate between the external surface of the wall and the central cavity for passage of removed bone and tissue through the wall into the central cavity. A holder is provided for transmitting torque to the reamer body about the cut axis. An alignment structure has at least two bars each extending between fixed ends, which are spaced from one another along the base, respectively. The bars are affixed to a cross-member in an H-shape to center the reamer body on the handle for controlled rotation of the reamer body about the cut axis.

Each of the above-listed further aspects of the present invention is most preferably an acetabular reamer having the alignment structure, which is attached to the handle by a bayonet catch.

An advantage of the present invention is a reamer with a static insertion profile that minimizes the size of the surgical incision, compared with conventional reamers, as well as providing a 3-dimensional tool contour that eases its surgical introduction into the bone cavity for reaming, all of the above while providing a precise shaping of the desired bone cavity.

Another advantage of a preferred reamer of the present invention is ease of extraction from the bone cavity through a minimally invasive surgical incision.

Yet another advantage is a reliable means of assembling various types of reamers to similar or different types of handle for controlled rotation of the reamer in the bone cavity. Such an advantage is particularly beneficial in surgical devices that require the reamer-handle connection to function together with a particular static insertion profile of the reamer.

Another advantage of a preferred reamer of the present invention its ready access for removal of debris for collection.

Other objects and advantages will become apparent to those skilled in the art, upon reviewing the Figures of the Drawings, in conjunction with the Detailed Description set forth further below, wherein references to numerals corresponds to like references in the Drawings.

BRIEF DESCRIPTION OF THE DRAWINGS

FIG. 20 is a partial assembly view, cut-away, schematically showing the H-shaped bar arrangement assembled within the bayonet catches of the handle of FIG. 19, with the bayonet pins engaged between the bars;

FIG. 21 is a perspective view of an alternatively preferred H-shaped bar assembly with rectangular cross-member for use with the reamer of FIG. 17 and a handle similar to FIGS. 19-20 that is optionally adapted for a recessed platen;

FIG. 22 is a top view of the alternative H-shaped bar construction of FIG. 21;

FIG. 23 is a side view of the H-shaped bar construction of FIGS. 21-22, shown assembled with a handle;

FIG. 24 is a bottom view of the H-shaped bar construction of FIGS. 21-22, shown assembled with a handle;

FIG. 25 is a top view of the H-shaped bar construction of FIGS. 21-22, shown assembled with a handle;

FIG. 26 is an isometric view of FIG. 25;

FIG. 27 is a bottom view of a reamer of the present invention having a cutting structure with a convex static insertion profile area as in FIGS. 4-7, showing an alternatively preferred alignment structure with a diametrically extending bar including a centering boss for connection with a handle;

FIG. 28 is a bottom view of a reamer of the present invention having a cutting structure with a convex static insertion profile area as in FIGS. 4-7, showing an alternatively preferred alignment structure with a diametrically extending plate including keyed polygonal centering opening for connection with a handle; and FIG. 29 is a bottom view of a reamer of the present invention having a cutting structure with a convex static insertion profile area as in FIGS. 4-7, showing an alternatively preferred alignment structure with a pair of keyed male centering members projecting inwardly from the bars toward the axis, respectively, for connection with a handle.

DETAILED DESCRIPTION

Figure 1:
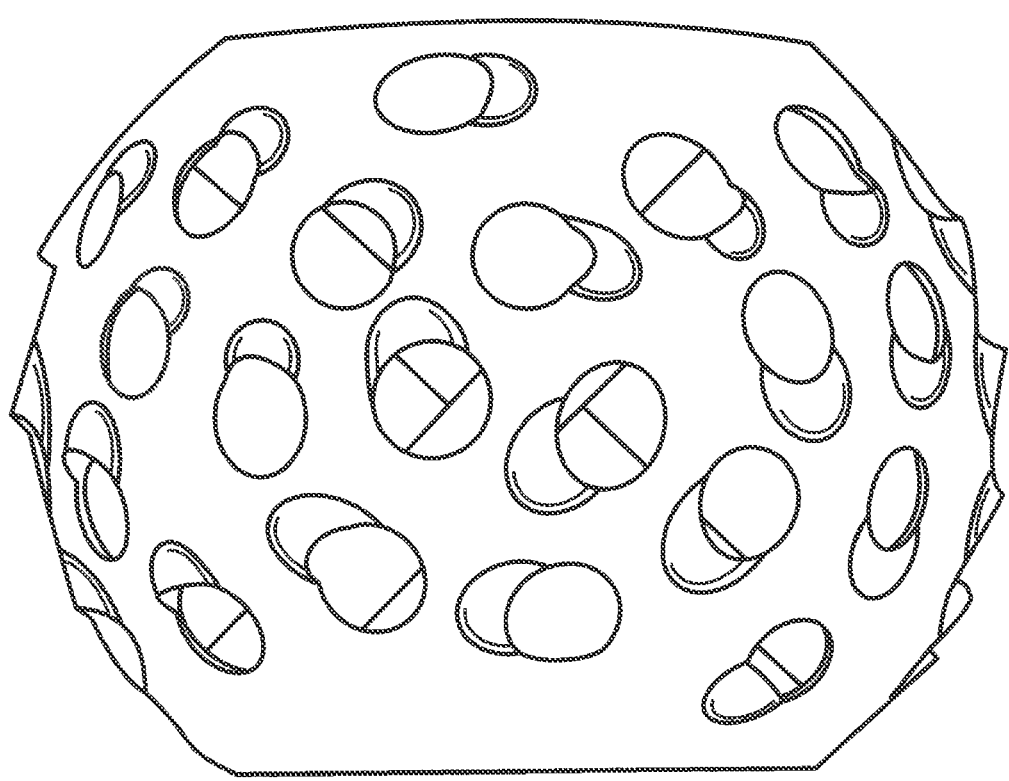
FIG. 1 is a top view of a prior art acetabular reamer having a static insertion profile area with two curved sides and two straight sides.
Figure 2:
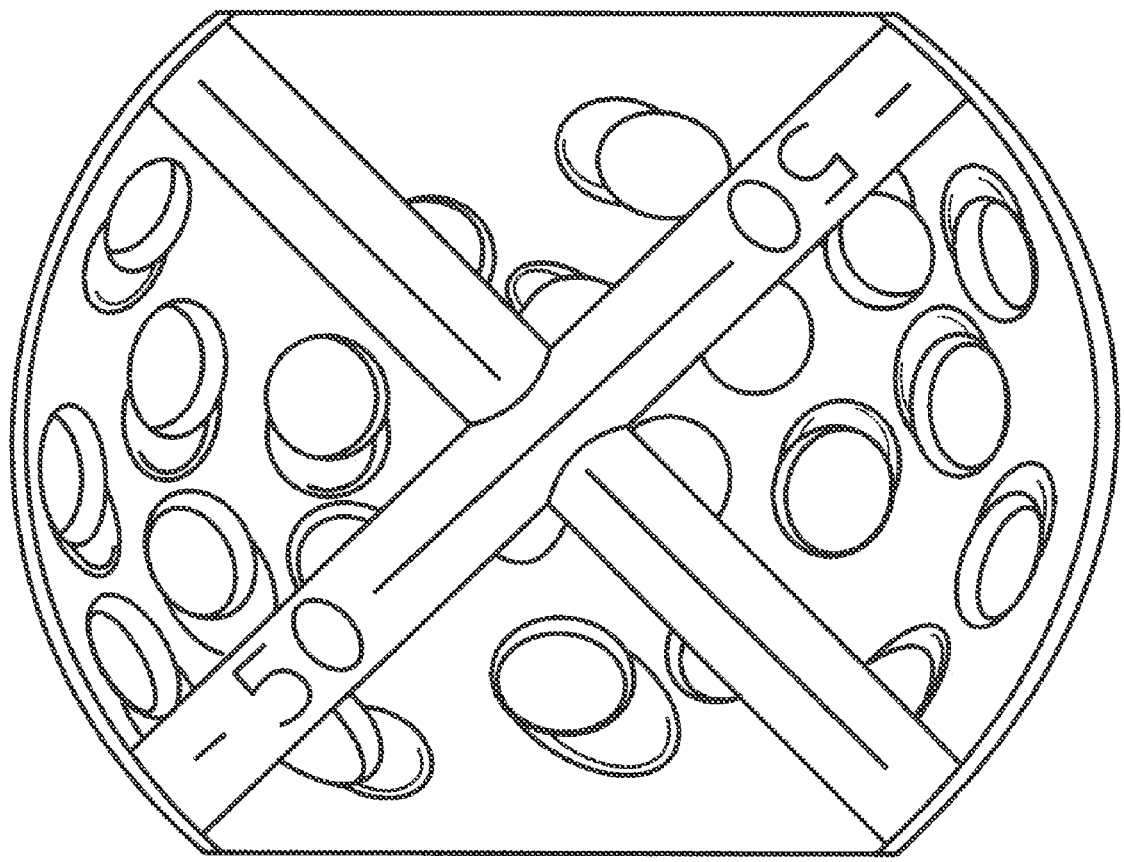
FIG. 2 is a bottom view of the reamer of FIG. 1.
Figure 3:
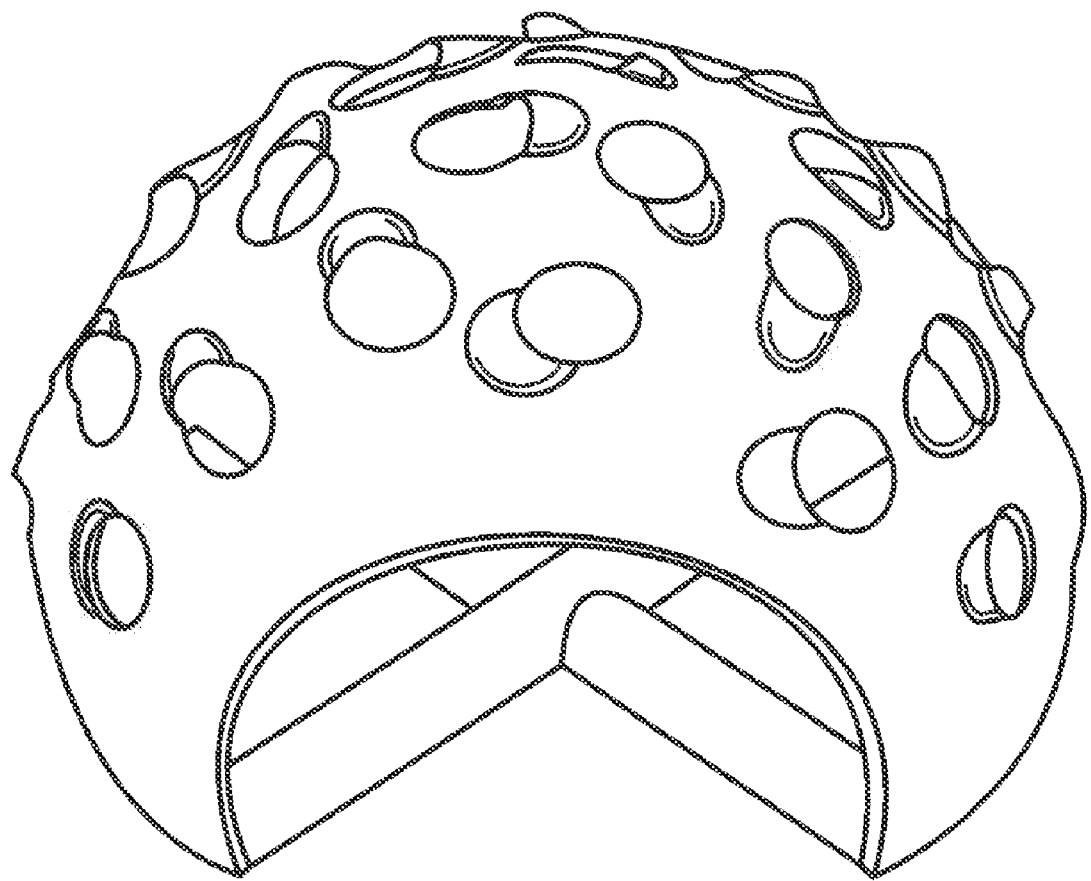
FIG. 3 is a perspective view of the reamer of FIG. 1.

Referring to FIGS. 1-3 a prior art acetabular reamer is generally shown, with a static insertion profile area having a pair of straight sides separated by a pair of curved sides. This construction is said to be minimally invasive, in terms of requiring a smaller surgical incision than required for conventional reamers having a circular or semi-circular static insertion profile, discussed in the inventors' above-mentioned earlier patents.

A present inventor has filed PCT/IB01/02676, entitled "Surgical Reamer" on Dec. 21, 2001 (Attorney Case 27), which discloses a reamer having a bladed construction with a static insertion profile area designed for introduction through a minimally invasive surgical incision. A present inventor has also filed U.S. Provisional Application No. 60/328,154, entitled "Acetabular Reamer", on Dec. 9, 2001 (Attorney Case No. 24), which describes a reamer with cutting sites constructed and presented along the rim of the reamer body, e.g., blades. The entire disclosures of the above-noted applications are incorporated by reference herein and relied-upon, copies being provided herewith.

Reference is now made in general to FIGS. 4-29. These show several aspects according to the present invention, in alternatively preferred embodiments of the contemplated reamers 10, as well as further aspects according to the present invention showing various connections for assembling such reamers to a handle as will be described.

Figure 14:
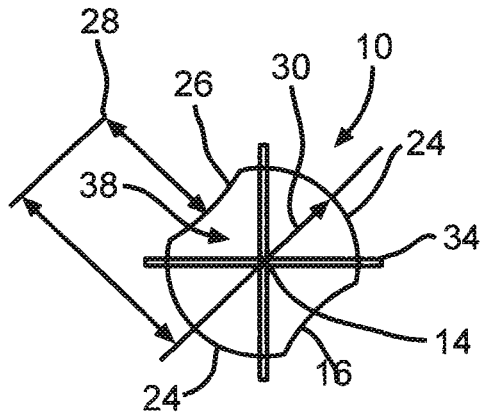
FIG. 14 is a bottom view of FIG. 12, showing an X-shaped arrangement of bars for connection with a handle, with blades extending outboard of pairs of banded base portions, the blades being aligned with the bar termini.

According to one aspect of the present invention, as shown in FIGS. 4-15 and 17, there is provided a surgical reamer 10 for cutting a bone socket (not shown). The reamer has a cutting structure 12 rotatable about a longitudinal axis 14, with a domed shell portion 16 having an outer surface 18 presenting multiple cutting sites for teeth 20 and an inner surface 22 for accumulation of debris. Shell 16 has a static insertion profile area being defined by a first curved portion 24 but preferably a pair of curved portions 24, 24, generated about a first radius 30 with a center that lies on the axis 14 (FIG. 14). A second curved portion, preferably a pair of second curved portions 26, 26 are generated about a center 28 (FIG. 14) that is spaced apart from the axis. The cutting structure 12 has a preferably circular dynamic profile area generated upon rotation. Both static insertion and dynamic profile areas lie transverse to the axis 14, with the static insertion profile area being smaller than the dynamic profile area.

In one or more preferred embodiments of the invention shown illustratively in FIGS. 4-15 and 17, the pair of first curved portions 24 preferably describes a diameter of the domed shell portion 16, the pair of first curved portions being situated in opposed relationship to one another with respect to the diameter coinciding with the first radius 30. The number of first curved portions 24 may be 2, 4 or some other even number.

Figure 10:
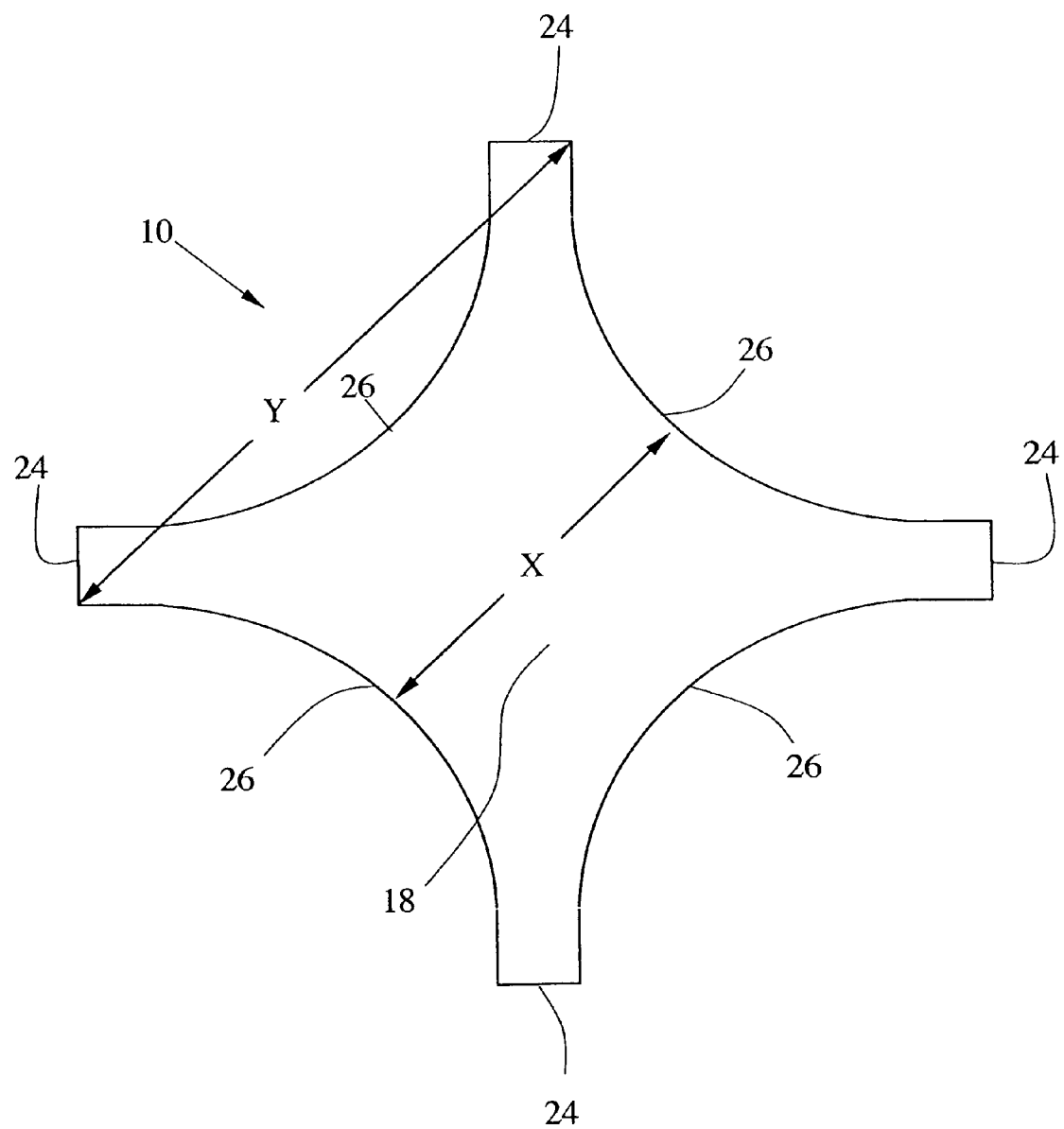
FIG. 10 is a top view of still another preferred reamer of the present invention, showing a cutting structure having a shell describing a convex, cruciform static insertion profile area, with a similar convex width (x) to FIG. 7.

In another preferred embodiment of the invention, the pair of second curved portions 26 is situated in opposed relationship from one another with respect to the shell 16. The pair of second curved portions 26 may be either convex (FIGS. 4-7) or concave (FIGS. 8-9), relative to the rotational axis 14; moreover, the curvature geometry may be described as circular or parabolic depending on design. The number of second curved portions 26 may be 2, 4 or some other even number, preferably corresponding to the number of first curved portions 24 noted above, with the pair(s) of first curved portions being separated from one another by the pair(s) of second curved portions, respectively. Thus the cutting structure 12 may present a partially circular convex or concave static insertion profile area, where one pair of first 24 and one pair of second 26 curved portions is provided. As shown in FIG. 10, the shell 16 may present a cruciform static insertion profile area where two pairs of first and second curved portions are chosen by design. A convex static insertion profile area is more beneficial in terms of introducing the reamer 10 through a less invasive surgical incision (not shown), whereas a concave static insertion profile area is designed for easier extraction of the reamer from the incision. The pairs of second curved portions 26 have a convex width (x) taken through the apex, which is less than the chordal dimension (y) between adjacent fixed ends of the respective bars of an alignment structure (not shown, which is X-shaped as illustrated by the alignment structure 38 of FIGS. 12-15.

Figure 15:
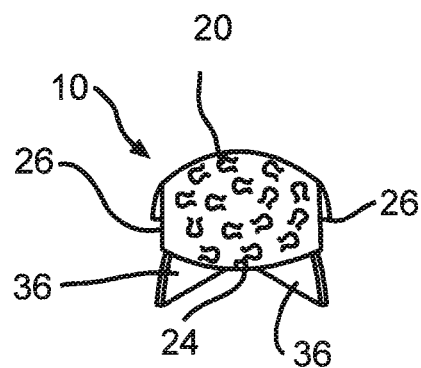
FIG. 15 is a side view of an alternative reamer of FIG. 12, shown having a toothed shell portion with a concave static insertion profile and an alternative bladed design without banded base portions.

In yet another preferred embodiment of the invention, shown by FIGS. 12-15, the shell 16 has a partially hemispherical domed 3-dimensional shape defining an apex aligned with the axis 14, and a pair of first curved portions 24 that respectively define a pair of diametrically opposed base portions spaced from the apex. It is further alternatively preferred that the base portions may be bands 32 and include bladed portions 34 to facilitate the reaming of a fully hemispherical, i.e., acetabular, bone cavity. Alternatively, the blades may form separate extensions 36 located below the shell 16, in the case of a more abbreviated shell, as shown in FIG. 15.

According to another aspect of the present invention illustrated in FIGS. 4-10 and 17, the shell 16 preferably defies a partially hemispherical domed 3-dimensional shape with an apex aligned with the axis 14. The shell 16 has a pair of first curved portions 24 that respectively define a pair of diametrically opposed base portions spaced from the apex. A mounting means preferably is an alignment structure 38 extending between the base portions and assembled with a handle 40 such as that illustratively shown in FIG. 19, for controlled rotation of the reamer 10. The handle 40 more preferably has bayonet catches 41 for receiving the alignment structure 38, as will be further described by way of illustration relative to FIGS. 17-21. The alignment structure 38 may be a single bar 42 with a centering boss 44 (FIG. 27) that may further optionally include a central aperture 46.

Alternatively, the alignment structure 38 may be a plate 50 with keyed centering aperture 52 (FIG. 28).

Figure 16:
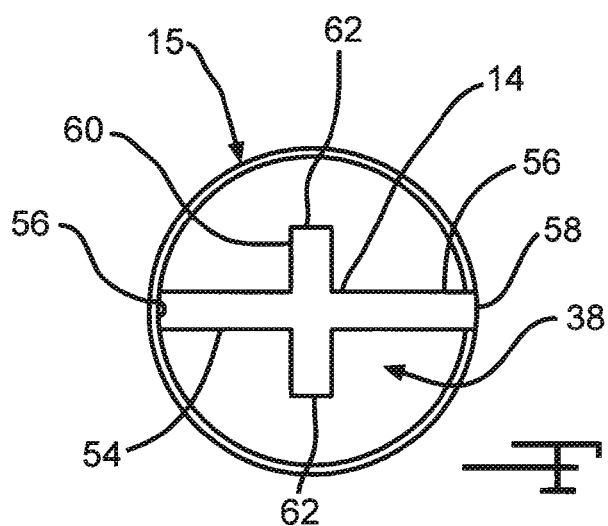
FIG. 16 is a bottom view of a reamer according to another aspect of the invention, showing a preferred cruciform arrangement of bars for connection of a conventional hemispherical domed cutting tool to a handle.

As depicted in FIG. 16, a shell 15 has an alignment structure 38 with a bar 54 having a pair of opposed terminal ends 56 fixed at the base 58, including a cross-member 60 having a pair of opposed free ends 62 and being of a lesser length than the bar. The cross-member 60 intersects the bar at the axis 14 to define a cruciform shape for attaching the reamer 10 to a handle. (see preferred bayonet catch 41 on e.g., a handle 40 similar to that of FIG. 19), while allowing removal of debris adjacent the free ends of the cross-member.

Still alternatively, in FIG. 29 the alignment structure 38 may be a pair of bars 64 spaced from one another on either side of the axis 14, with a pair of keyed male centering members 66 projecting inwardly from the bars toward the axis, respectively. A corresponding mechanism in the handle (not shown) engages the male centering members 66.

Figure 4:
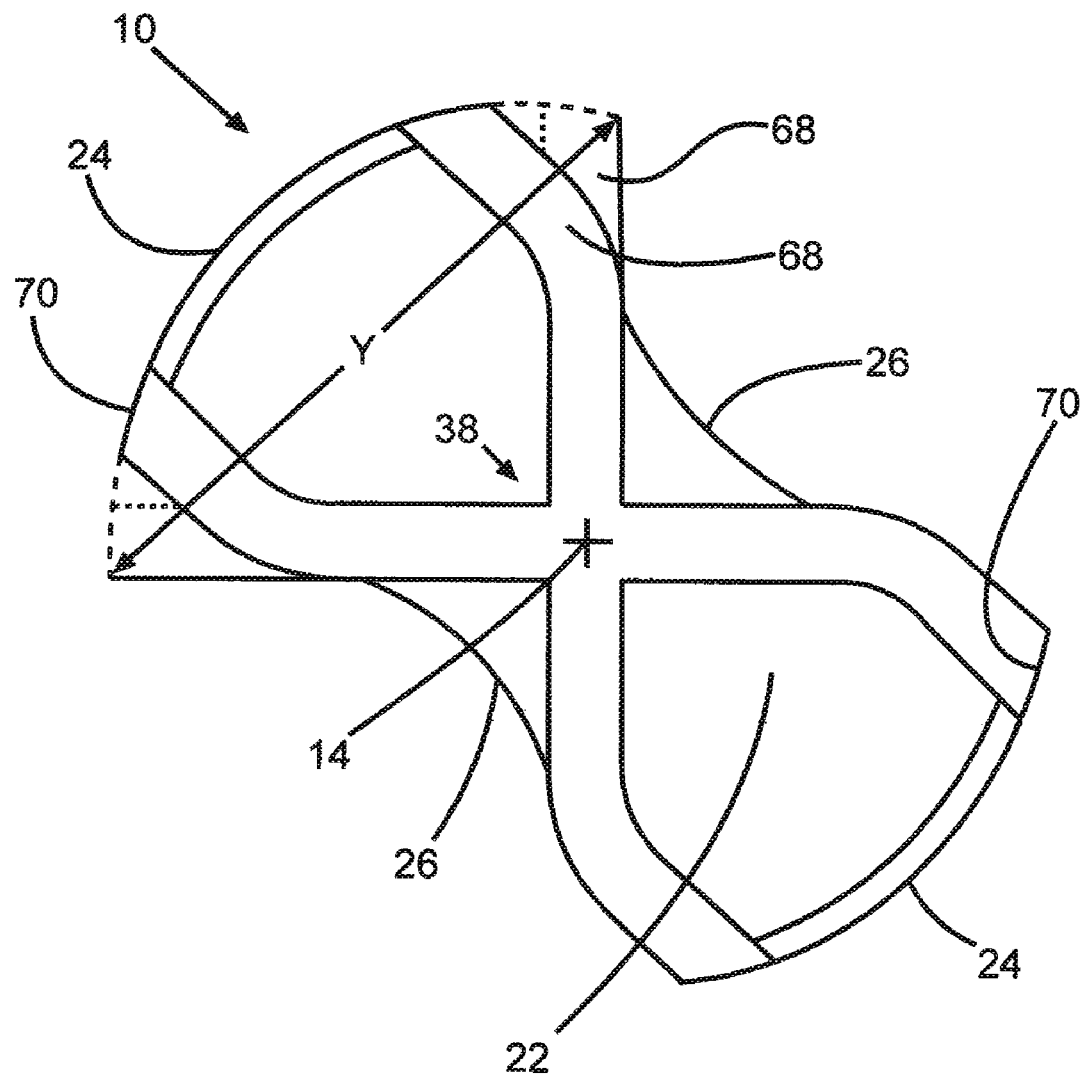
FIG. 4 is a bottom view of a preferred reamer according to the present invention in one of its aspects, showing a cutting structure with a shell having a further preferred convex static insertion profile area for minimally invasive introduction through a surgical incision, and also showing an alternatively preferred Y-shaped arrangement of bars for connection to a handle.
Figure 5:
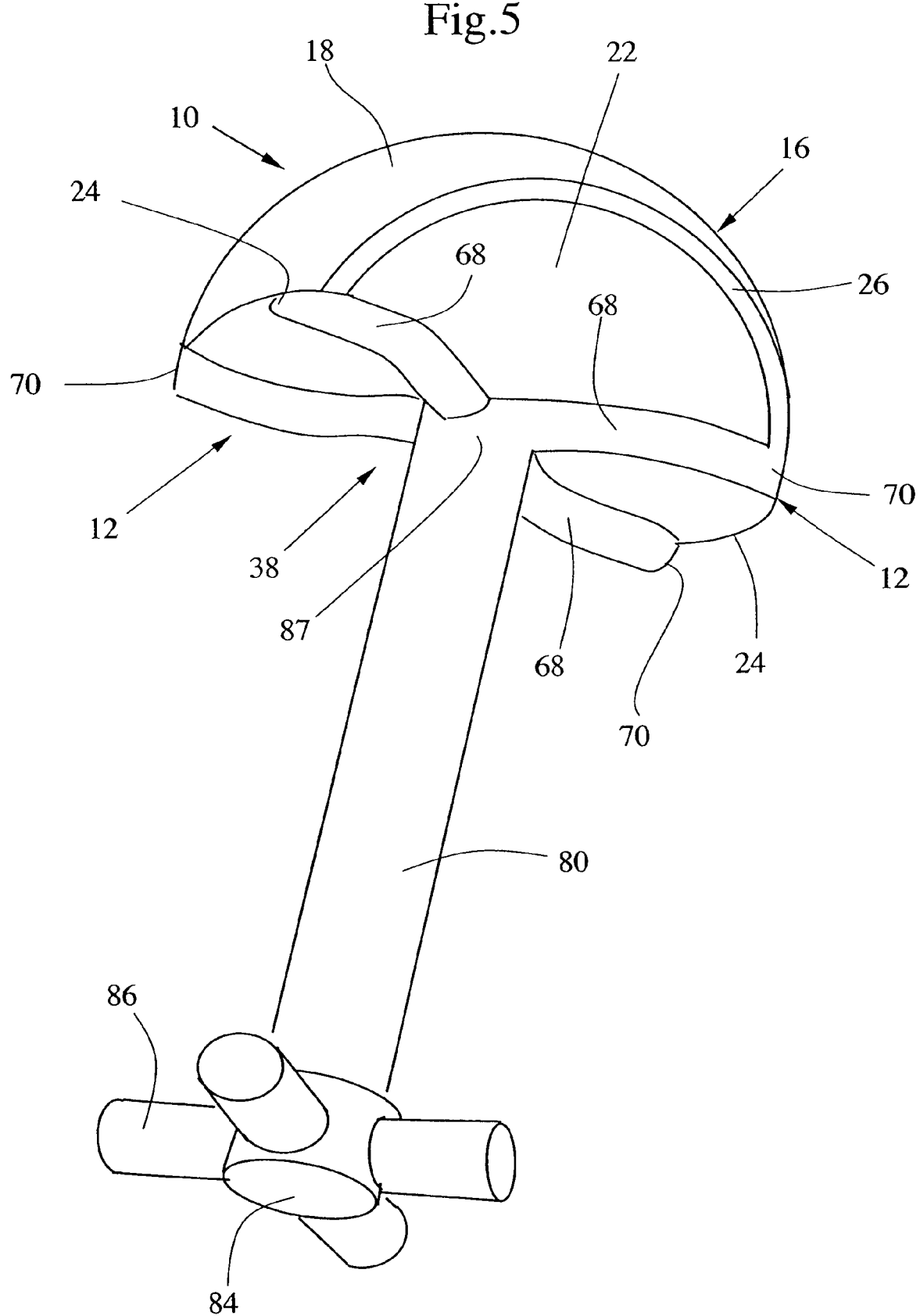
FIG. 5 is a perspective view of the reamer of FIG. 4, showing the bars centrally affixed to an optional drive shaft with a free end for connection to the handle.
Figure 6:
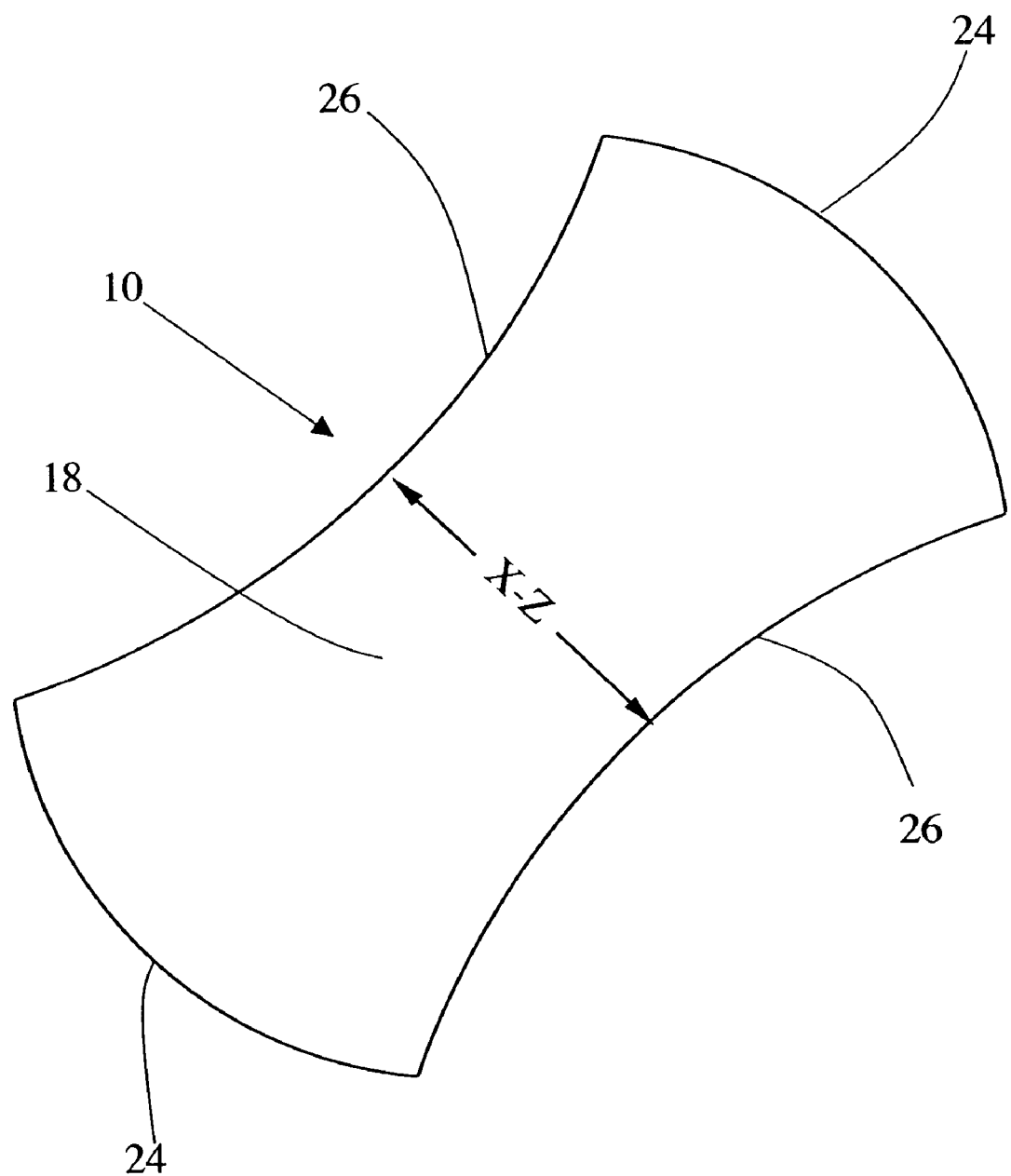
FIG. 6 is a top view of the reamer of FIG. 4, showing the convex width (x–z) of the static insertion profile taken through the rotational axis.
Figure 7:
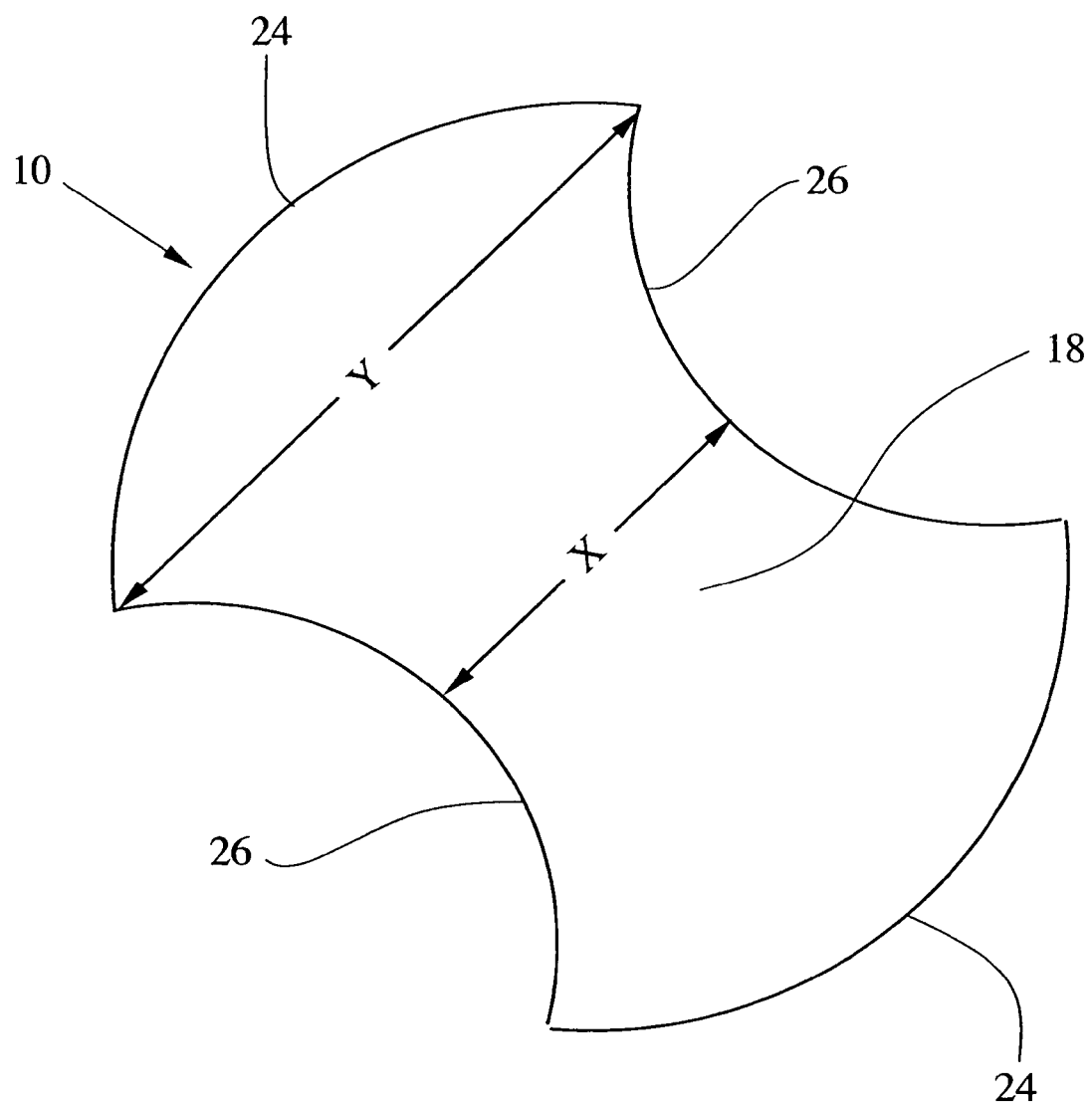
FIG. 7 is a top view of a reamer similar to FIG. 4, with an alternatively preferred static insertion profile area that is larger in convex width (x) through the rotational axis, compared to the reamer of FIG. 4.
Figure 8:
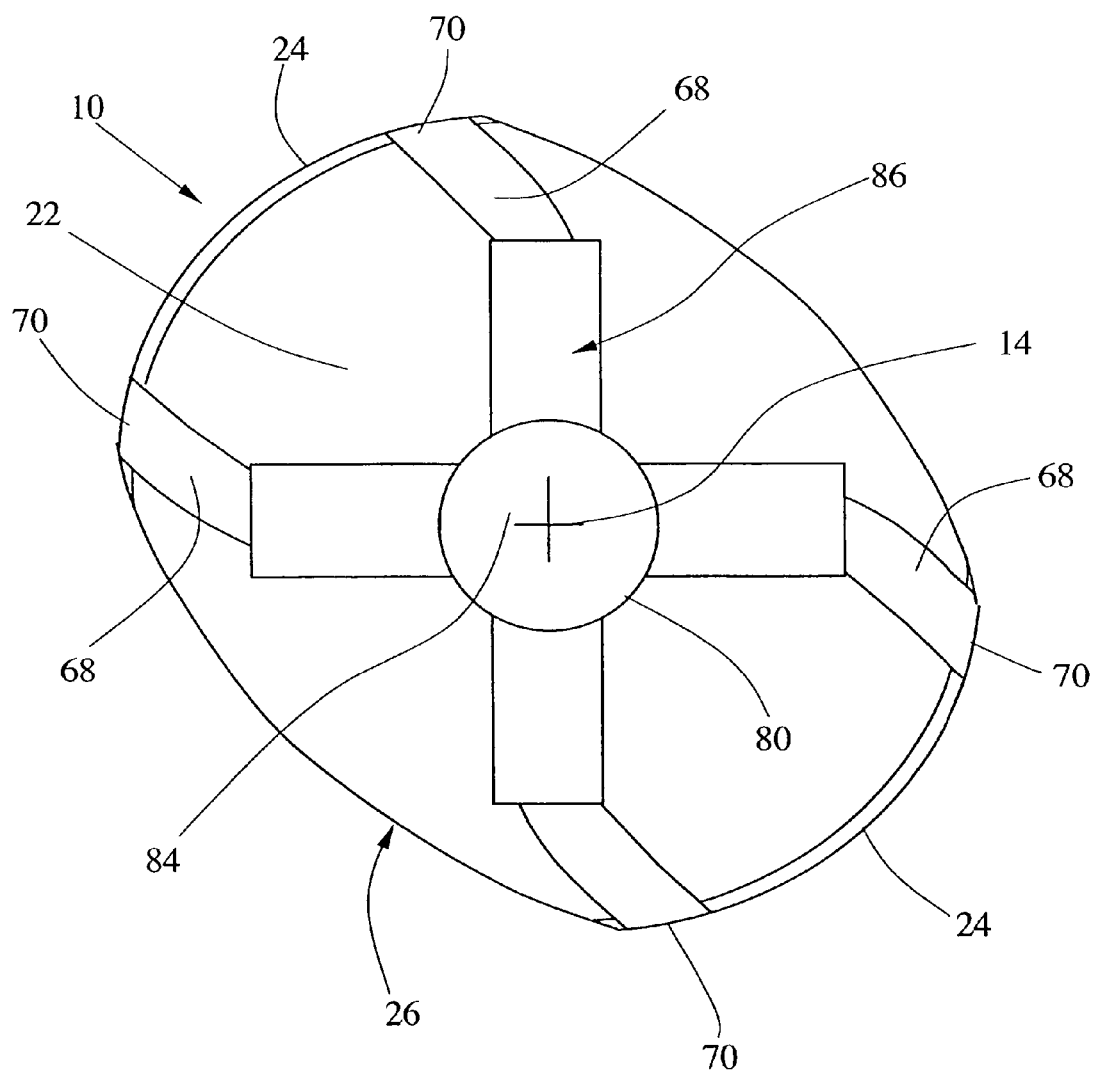
FIG. 8 is a bottom view of another preferred reamer according to the present invention, showing a cutting structure with a shell having a further preferred concave static insertion profile area for minimally invasive extraction through a surgical incision, and also showing the alternatively preferred Y-shaped arrangement of bars similar to FIG. 4 together with optional drive shaft as in FIG. 5.
Figure 9:
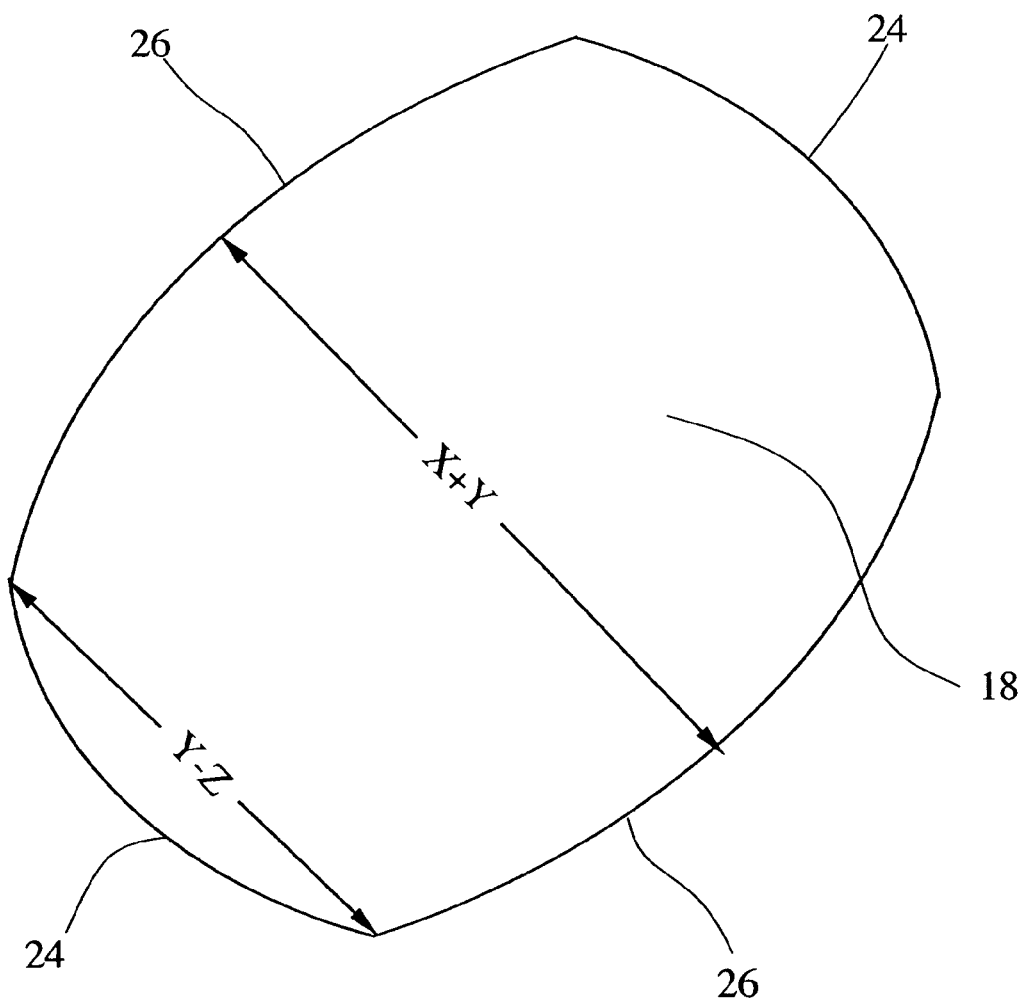
FIG. 9 is a top view of FIG. 8, showing the concave width (x+z) of the static insertion profile.
Figure 11:
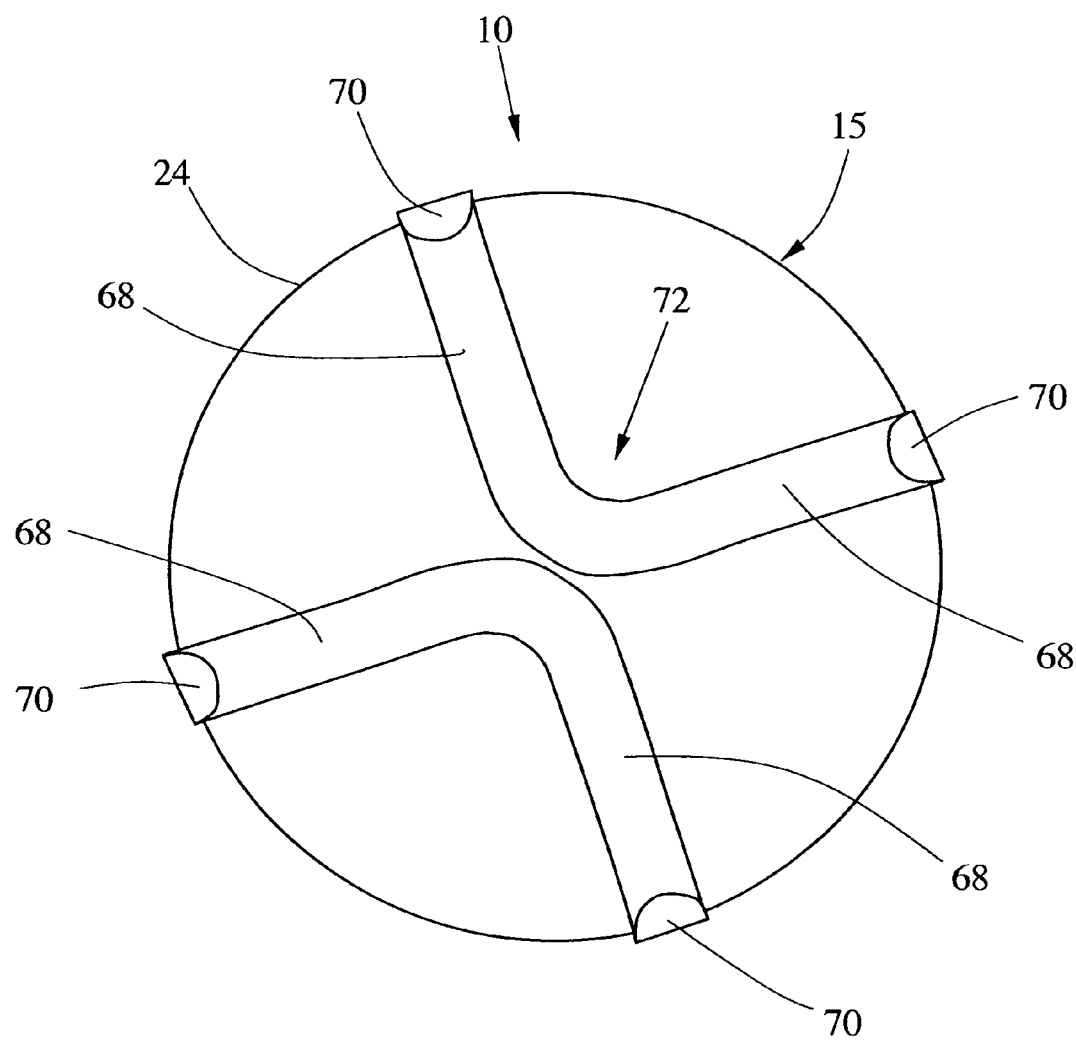
FIG. 11 is a bottom view of a preferred reamer of the present invention in another of its aspects, showing an arrangement of converging curved bars for connection to a driver handle, in combination with a prior art tool having a circular static insertion profile area.
Figure 12:
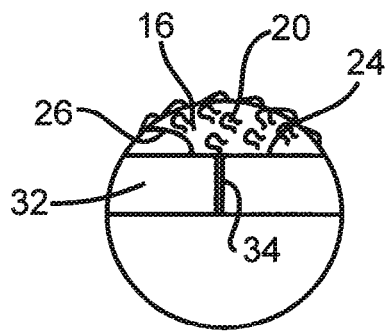
FIG. 12 is a side view of a further preferred reamer of the present invention having a toothed shell portion with a convex static insertion profile and an alternatively preferred bladed portion, also indicating the centers of the convex curved portions.
Figure 13:
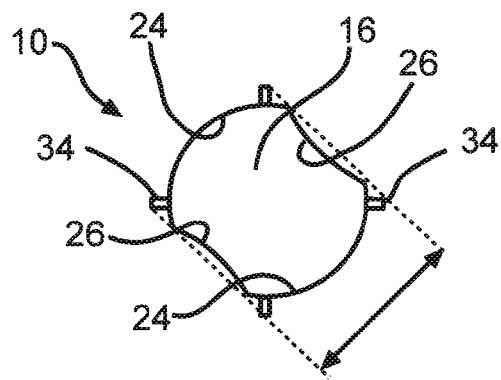
FIG. 13 is a top view of FIG. 12.
Figure 17:
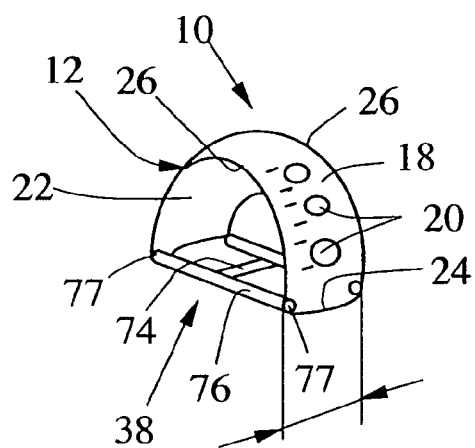
FIG. 17 is a perspective view of a reamer of the present invention, showing a preferred H-shaped arrangement of bars for connection of a further preferred cutting structure having convex width (x), to a handle.
Figure 18:
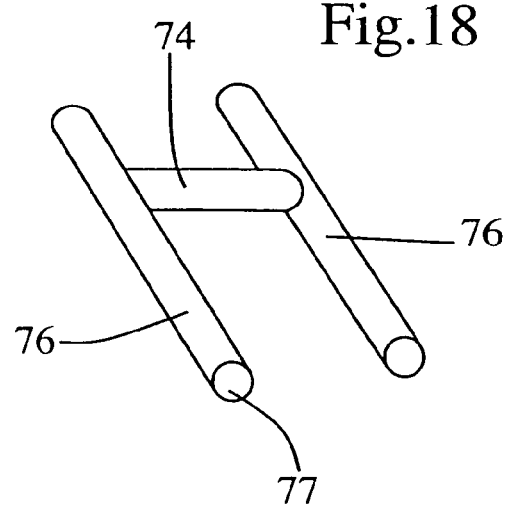
FIG. 18 is a perspective view of the H-shaped bar arrangement shown in the reamer of FIG. 17.
Figure 19:
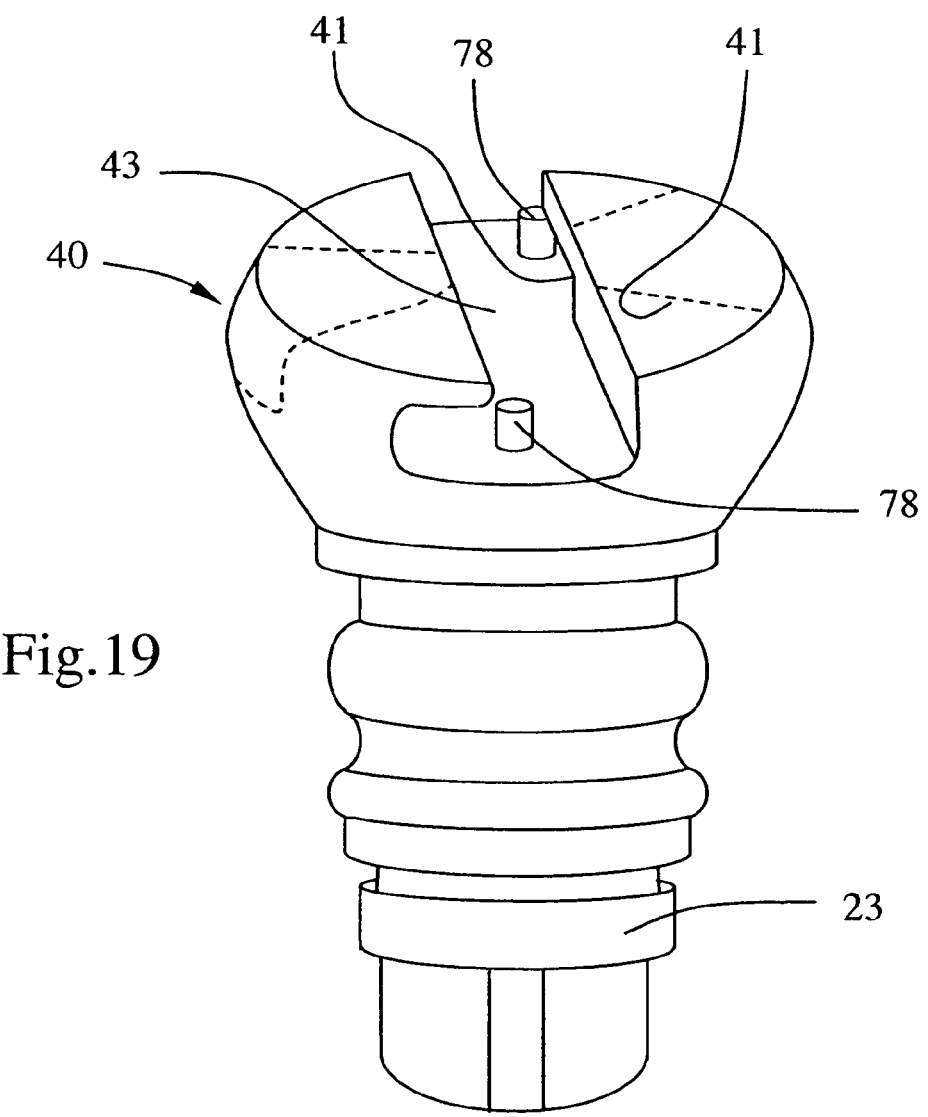
FIG. 19 is a perspective view of a handle for use with the reamer of FIG. 17, showing a bayonet catch mechanism adapted to receive the H-shaped bar arrangement of FIGS. 17-18 and optionally showing a phantom adaptation for alternatively preferred X-shaped (FIG. 14), Y-shaped (FIG. 4) and cruciform (FIG. 16) bar arrangements of the inventive reamer.

Likewise, in still another alternative embodiment, there is provided in FIG. 11 a novel connection for a conventional hemispherical shell 15, which can also be used with a shell 16 of FIGS. 4-10, for example. A pair of bars 68 each having opposed terminal ends 70, with adjacent ones of the ends being spaced from one another along each first curved portion 24 that forms a corresponding base portion, including a centering structure 72 located on the pair of bars for attachment to a handle (FIG. 19). In FIG. 17, a centering structure 38 is preferably a cross-member 74, which together with a pair of bars 76 forms an H-shape for receiving, between the bars, one or more longitudinal pins 78 from a bayonet catch 41 on the handle 40. In FIGS. 4-11, the alignment structure 38 is preferably a pair of curved bars 68. In FIGS. 4-6 these bars 68 each are generally formed in an S-shape. The convergent bars 68 of FIG. 11 are non-intersecting and U-shaped presenting a generally hourglass configuration allowing the bars to be directly received by corresponding bayonet catches 41 of the handle 40 (FIG. 19). In FIGS. 4-10, the bars 68 are intersecting and have a generally Y-shaped form defining a chordal dimension (y–z) between their respective adjacent fixed ends 70, versus a theoretical X-shaped arrangement (shown in phantom in FIG. 4) that represents a larger chordal dimension (y). Alternatively, a shaft 80 is provided having a fixed end 82 joined to the bars 68 adjacent the rotational axis 14 and extending longitudinally toward the handle (not shown), the shaft having a free end 84 with radial spokes 86 for receipt in corresponding bayonet catches 41 of the handle.

According to a further aspect of the present invention shown in FIG. 16, there is provided a hollow reamer body in the form of shell 15 having a wall portion with an outer external surface 18, a pair of opposed base portions formed by the pair of first curved portions 24 and an apex defining a cut axis. The wall defines a central cavity and a plurality of passageways through the wall presenting cutting sites containing teeth 20. The passageways communicate between the external surface 18 and the central cavity, for passage of removed bone and tissue through external surface into the central cavity. A holder (FIG. 19) is provided for transmitting torque to the reamer 10, for rotation of the reamer about the cut axis 14. An alignment structure 38 is provided on the reamer 10 for assembly with the handle 40, including a first bar 54 extending between the first curved 24 and a second bar 60 that intersects the first bar along the cut axis 14. The second bar further includes opposed free ends 62 and has a shorter length than the first bar 54 to allow removal of debris there around, the first 54 and second 60 bars together forming a cruciform shape allowing the bars to be attached to the handle for controlled rotation of the reamer body.

According to yet a further aspect of the present invention shown in FIG. 11, a surgical reaming assembly includes a hollow reamer body having a wall portion with an external surface, a pair of opposed base portions and an apex defining a cut axis. The wall defines a central cavity and a plurality of passageways through the wall presenting cutting sites. The passageways communicate between the external surface of the wall and the central cavity for passage of removed bone and tissue through the wall into the central cavity. A holder (shown illustratively at 40 in FIG. 19) is provided for transmitting torque to the reamer body about the cut axis 14. An alignment structure 38 is provided for assembling the reamer 10 to the handle 40, having a pair of non-intersecting curved bars 68 each extending between a pair of fixed ends 70 respectively located on the opposed base portions. The bars 68 converge in a direction toward the cut axis 14 and are attached to the handle 40 for controlled rotation of the reamer body 10.

According to still a further aspect of the present invention shown in FIGS. 17-20, and FIGS. 22-26, a surgical reaming assembly includes a hollow reamer body 10 having a wall with an external surface 18, a base and an apex defining a cut axis. A wall forming a shell 16 contains a central cavity and has a plurality of passageways through the wall presenting cutting sites with teeth 20. The passageways communicate between the external surface 18 and the central cavity for passage of removed bone and tissue through the shell 16 into the central cavity. A holder 40 is provided for transmitting torque to the reamer 10 about the cut axis 14. An alignment structure 38 has a pair of bars 76, each extending between respective pairs of fixed ends 77. Adjacent ends 77 of the bars 76 are spaced from one another along the base, respectively. The bars 76 are affixed to a cross-member 74 in an H-shape on platen 43 with pin 45 to center the reamer 10 on the handle 40 for controlled rotation of the reamer about the cut axis 14.

Each further aspect of the present invention, as respectively shown in FIGS. 11, 16 and 17-20, is most preferably an acetabular reamer 10 having the alignment structure 38, which is attached to the handle (shown at 40 in FIG. 19) by a bayonet catch 41. Likewise, each further aspect of the invention may be utilized to assemble a conventional domed reamer body (FIG. 11). Moreover, a cutting structure 12 of the one or another aspects of the present invention may be utilized, in order to allow a less invasive surgical incision.

Multiple variations and modifications are possible in the embodiments of the invention described here. Although certain illustrative embodiments of the invention are shown and described here, a wide range of modifications, changes, and substitutions is contemplated in the foregoing disclosure. In some instances, certain features of the present invention may be employed without a corresponding use of the other features. Accordingly, it is appropriate that the foregoing description be construed broadly and understood as being given by way of illustration and example only, the spirit and scope of the invention being limited only by one, another or a further aspect of the appended claims.

What is claimed is:

1. A surgical reamer for cutting a bone socket, comprising:
   a) a hollow dome comprising:
      i) a dome portion of a hemisphere extending from an apex to a lower edge, the dome portion being rotatable about a longitudinal axis that is perpendicular to a theoretical equatorial plane of the hemisphere and that passes through the apex of the dome portion, wherein the dome portion has an outer surface presenting multiple cutting sites , comprising apertures suitable for passing debris into a cavity defined by an inner surface of the dome where the debris may accumulate;
      ii) at least two opposed first edge portions of the lower edge residing on the theoretical equatorial plane, wherein a second theoretical plane perpendicular to the equatorial plane intersects the longitudinal axis and two of the at least two first edge portions residing on the theoretical equatorial plane; and
      iii) at least two continuously curved second edge portions of the lower edge spaced from the theoretical equatorial plane toward the apex, wherein at least one second edge portion resides on opposite sides of the second theoretical plane disposed between and connected to two of the first edge portions; and
   b) an alignment structure connected to the inner surface of the dome portion for detachably connecting the hollow dome to a drive mechanism.

2. The reamer of claim 1 wherein the at least two opposed first edge portions are curved portions.

3. The reamer of claim 2 wherein the at least two first curved portions intersect the theoretical equatorial plane and describe a diameter of the hollow dome.

4. The reamer of claim 1 wherein the second curved portions are opposed to one another on opposite sides of the second theoretical plane.

5. The reamer of claim 1 wherein the at least two second curved portions are concave relative to the rotational axis.

6. The reamer of claim 1 wherein there are a plurality of first curved portions and a plurality of second curved portions, and wherein the number of first curved portions equals the number of second curved portions.

7. The reamer of claim 6 wherein the number of first curved portions is 2 or 4.

8. The reamer of claim 1 wherein a dynamic profile area of the reamer is circular.

9. The reamer of claim 1 wherein the alignment structure comprises:
   a) a first bar having a first length extending to opposed terminal ends connected to the inner surface of the dome portion at locations along the second theoretical plane; and b) a cross-member having opposed free ends and being of a lesser length than the bar, the cross-member intersecting the bar at the axis to define a cruciform shape for receipt by a bayonet catch on a holder, while allowing removal of debris adjacent the free ends of the cross-member.

10. A surgical reaming assembly comprising:
   a) a hollow dome comprising:
      i) a dome portion of a hemisphere extending from an apex to a lower edge, the dome portion being rotatable about a longitudinal axis that is perpendicular to a theoretical equatorial plane of the hemisphere and that passes through the apex of the dome portion, wherein the dome portion has an outer surface presenting multiple cutting sites comprising apertures suitable for passing debris into a cavity defined by an inner surface of the dome where the debris may accumulate;
      ii) at least two opposed first edge portions of the lower edge residing on the theoretical equatorial plane, wherein a second theoretical plane perpendicular to the equatorial plane intersects the longitudinal axis and two of the at least two first edge portions residing on the theoretical equatorial plane; and
      iii) at least two continuously curved second edge portions of the lower edge spaced from the theoretical equatorial plane toward the apex, wherein at least one second edge portion resides on opposite sides of the second theoretical plane disposed between and connected to two of the first edge portions; and
   b) an alignment structure for detachably connecting the hollow dome to a drive mechanism, wherein the alignment structure comprises:
      i) a first bar having a first length extending to opposed first ends connected to the inner surface of the dome portion at locations along the second theoretical plane;
      ii) a second bar bisecting the first bar, wherein the second bar has a second length extending to opposed second ends that reside intermediate the theoretical equatorial plane and the apex of the dome portion and that are spaced inwardly from the second edge portions of the dome; and
      iii) wherein the first length of the first bar is greater than the second length of the second bar; and
   c) a holder that is detachably connectable to the alignment structure for transmitting rotational torque to the hollow dome.

11. The reamer of claim 1 wherein the second theoretical plane bisects the dome portion along the first edge portions residing on the theoretical equatorial plane.

12. The reamer of claim 1 wherein the alignment structure comprises:
   a) a first bar having a first length extending to opposed first ends connected to the inner surface of the dome portion at locations along the second theoretical plane;
   b) a second bar intersecting the first bar, wherein the second bar has a second length extending to opposed second ends that reside intermediate the theoretical equatorial plane and the apex of the dome portion and that are spaced inwardly from the second edge portions of the dome; and
   c) wherein the first length of the first bar is greater than the second length of the second bar.

13. The reamer of claim 1 wherein the first bar is aligned along the second theoretical plane and intersects the dome portion along the longitudinal axis and along the first edge portions residing on the theoretical equatorial plane.

14. The reamer of claim 1 wherein the first bar is aligned along the second theoretical plane, intersecting the longitudinal axis and bisecting the first edge portions.

15. The reamer of claim 1 wherein second bar intersects the first bar at a right angle.

16. The reamer of claim 1 wherein the opposed ends of the first bar are connected to the inner surface of the dome portion at locations along the second theoretical plane and spaced from the theoretical equatorial plane toward the apex.

17. The reamer of claim 1 wherein the second bar bisects the first bar.

18. A surgical reaming assembly comprising:
   a) a hollow dome comprising:
      i) a dome portion of a hemisphere extending from an apex to a lower edge, the dome portion being rotatable about a longitudinal axis that is perpendicular to a theoretical equatorial plane of the hemisphere and that passes through the apex of the dome portion, wherein the dome portion has an outer surface presenting multiple cutting sites comprising apertures suitable for passing debris into a cavity defined by an inner surface of the dome where the debris may accumulate;
      ii) at least two opposed first edge portions of the lower edge residing on the theoretical equatorial plane, wherein a second theoretical plane perpendicular to the equatorial plane intersects the longitudinal axis and two of the at least two first edge portions residing on the theoretical equatorial plane; and
      iii) at least two continuously curved second edge portions of the lower edge spaced from the theoretical equatorial plane toward the apex, wherein at least one second edge portion resides on opposite sides of the second theoretical plane disposed between and connected to two of the first edge portions; and
   b) an alignment structure for detachably connecting the hollow dome to a drive mechanism, wherein the alignment structure comprises:
      i) a first bar having a first length extending to opposed first ends connected to the inner surface of the dome portion at locations along the second theoretical plane;
      ii) a second bar bisecting the first bar, wherein the second bar has a second length extending to opposed second ends that reside intermediate the theoretical equatorial plane and the apex of the dome portion and that are spaced inwardly from the second edge portions of the dome; and
      iii) wherein the first length of the first her is greater than the second length of the second bar.

* * * * *